US012588813B2

(12) United States Patent
Wang et al.

(10) Patent No.:  US 12,588,813 B2
(45) Date of Patent:      Mar. 31, 2026

(54) OPTICAL SYSTEM AND OPERATING METHOD THEREOF

(71) Applicant: Crystalvue Medical Corporation, Taoyuan City (TW)

(72) Inventors: William Wang, Taoyuan City (TW); Hsuan-Hao Chao, Tainan City (TW); Sung-Yang Wei, New Taipei City (TW); Chung-Cheng Chou, Luzhu Township (TW)

(73) Assignee: Crystalvue Medical Corporation, Taoyuan City (TW)

( * ) Notice: Subject to any disclaimer, the term of this patent is extended or adjusted under 35 U.S.C. 154(b) by 630 days.

(21) Appl. No.: 17/984,320

(22) Filed: Nov. 10, 2022

(65) Prior Publication Data

US 2023/0148861 A1     May 18, 2023

Related U.S. Application Data

(60) Provisional application No. 63/279,854, filed on Nov. 16, 2021.

(51) Int. Cl.
| | |
|---|---|
| *A61B 3/12* | (2006.01) |
| *A61B 3/00* | (2006.01) |
| *A61B 3/10* | (2006.01) |
| *A61B 3/14* | (2006.01) |

(52) U.S. Cl.
CPC .......... *A61B 3/1225* (2013.01); *A61B 3/0008* (2013.01); *A61B 3/102* (2013.01); *A61B 3/145* (2013.01)

(58) Field of Classification Search
CPC ..... A61B 3/1225; A61B 3/0008; A61B 3/102; A61B 3/145

USPC ......................................................... 351/208
See application file for complete search history.

(56) References Cited

U.S. PATENT DOCUMENTS

| | | | | |
|---|---|---|---|---|
| 7,800,759 | B2* | 9/2010 | Lai ........................ | A61B 3/1005 356/497 |
| 2007/0159596 | A1* | 7/2007 | Fukuma ............... | G01N 21/359 351/206 |
| 2010/0110377 | A1* | 5/2010 | Maloca ................. | A61B 3/102 351/208 |
| 2012/0140172 | A1* | 6/2012 | Torii ........................ | A61B 3/14 351/206 |

(Continued)

FOREIGN PATENT DOCUMENTS

| | | | | |
|---|---|---|---|---|
| CN | 109091294 | A | * 12/2018 | ......... A61F 9/00821 |

OTHER PUBLICATIONS

CN-109091294-A—English translation—Sun—Dec. 28, 2018.*

*Primary Examiner* — Sharrief I Broome
(74) *Attorney, Agent, or Firm* — Patterson + Sheridan, LLP

(57) ABSTRACT

An optical system and an operating method thereof are disclosed. The optical system includes a light source device, a gaze module and a fundus detection device. The light source device includes a light source module, a light intensity modulation module and a lens module. The light source module is used to emit a therapy light to an eye. The light intensity modulation module is used to modulate an intensity of the therapy light. The lens module is used to control a depth of the therapy light. The gaze module is used to be gazed by the eye to fix a fundus of the eye. The fundus detection device and the light source device are integrated to detect the fundus to obtain a fundus image.

20 Claims, 10 Drawing Sheets

(56)  References Cited

U.S. PATENT DOCUMENTS

| 2012/0229765 A1* | 9/2012 | Makihira | A61B 3/102 |
| | | | 351/246 |
| 2014/0333898 A1* | 11/2014 | Boate | A61B 3/0008 |
| | | | 351/221 |
| 2015/0305615 A1* | 10/2015 | Jackson | A61B 3/063 |
| | | | 351/239 |
| 2015/0327762 A1* | 11/2015 | Isogai | A61B 3/1005 |
| | | | 351/246 |
| 2016/0157713 A1* | 6/2016 | Yoshida | G01N 21/4795 |
| | | | 351/206 |
| 2016/0317031 A1* | 11/2016 | Yang | A61B 3/13 |
| 2018/0310819 A1* | 11/2018 | Boss | A61B 3/0025 |
| 2019/0133436 A1* | 5/2019 | Arikawa | A61B 3/0083 |
| 2019/0223711 A1* | 7/2019 | Mikaelian | A61B 3/0008 |
| 2020/0297206 A1* | 9/2020 | Zakharov | A61B 5/6803 |

* cited by examiner

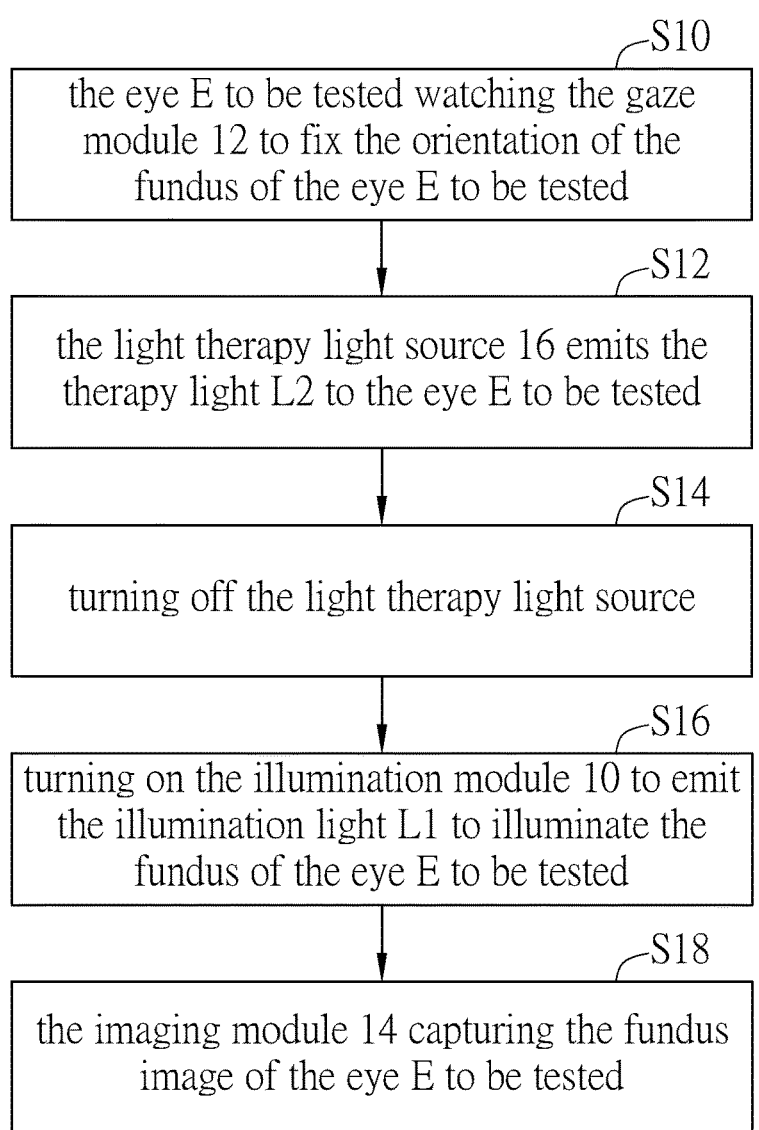

S10 the eye E to be tested watching the gaze module 12 to fix the orientation of the fundus of the eye E to be tested

S12 the light therapy light source 16 emits the therapy light L2 to the eye E to be tested

S14 turning off the light therapy light source

S16 turning on the illumination module 10 to emit the illumination light L1 to illuminate the fundus of the eye E to be tested

S18 the imaging module 14 capturing the fundus image of the eye E to be tested

FIG. 3

S110 the photosensitive module that can detect the
detection light and the therapy light is disposed in
the optical path, and is ready to start calibration

S112 moving the detection light with the detection light scanning module,
scanning a series of light spots on the photosensitive module in sequence,
and recording the coordinates of the detection light scanning range

S114 using the therapy light scanning module to move the therapy light, scanning
a series of light spots on the photosensitive module in sequence, and
recording the coordinates of the therapy light scanning range

S116 recording the coordinates of the scanning range of the detection light
and the coordinates of the scanning range of the therapy light and
aligning the two to complete the calibration; and

S118 the therapy light scanning module can move independently of
the detection light scanning module to treat a specific position
within the visual field of the eye to be tested

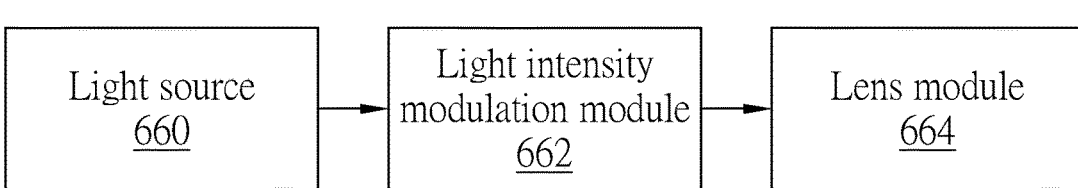

| Light source 660 | → | Light intensity modulation module 662 | → | Lens module 664 |

FIG. 12

OPTICAL SYSTEM AND OPERATING METHOD THEREOF

BACKGROUND OF THE INVENTION

1. Field of the Invention

The invention relates to an optical system; in particular, to an optical system and an operating metho thereof applied to eyes.

2. Description of the Prior Art

Low-intensity laser light therapy is a method of treating eye diseases, such as macular degeneration, primary open-angle glaucoma or retinitis pigmentosa. By irradiating the eyes with hand-held or fixed low-intensity infrared lasers (670 nm or 780 nm, 10 mW or less), the blood vessels of the eyes can be dilated, and the blood circulation of the retina and choroid tissue can be improved, thereby reducing the symptoms of ocular tissue hypoxia and ischemia caused by glaucoma, macular and retinopathy.

Furthermore, low-intensity laser illumination can also reduce the generation of ocular fluid and enhance the efficiency of fluid discharge, thereby reducing intraocular pressure, thereby reducing glaucoma symptoms. In addition, mitochondrial dysfunction is considered to be a main pathological factor of glaucoma. Some papers have pointed out that irradiating eye cells with low-intensity lasers can stimulate mitochondria to synthesize adenosine triphosphate (ATP) to increase mitochondrial function, thereby improving glaucoma symptoms.

However, since the eyes naturally vibrate, it greatly increases the difficulty of locking a specific position, so that the conventional light therapy can only roughly illuminate a large area of the fundus instead of scanning or locking detailed areas of the fundus for intensive treatment. In addition, the therapeutic effect after phototherapy still needs to be determined by taking a fundus image of the area with other instruments, which is quite time-consuming and inconvenient.

Therefore, the above-mentioned problems encountered in the prior art still need to be further solved.

SUMMARY OF THE INVENTION

Therefore, the invention provides an optical system and an operating method thereof applied to eyes to solve the above-mentioned problems of the prior arts.

A preferred embodiment of the invention is an optical system. In this embodiment, the optical system includes a light source device, a gaze module and a fundus detection device. The light source device includes a light source module, a light intensity modulation module and a lens module. The light source module is used to emit a therapy light to an eye. The light intensity modulation module is used to modulate an intensity of the therapy light. The lens module is used to control a depth of the therapy light. The gaze module is used to be gazed by the eye to fix a fundus of the eye. The fundus detection device and the light source device are integrated to detect the fundus to obtain a fundus image.

In an embodiment, when the light source module only includes a single light source, the single light source needs to be matched with a light scanning module to modulate the therapy light to irradiate to a specific position and range of the eye.

In an embodiment, when the light source module includes a plurality of light sources arranged in an array, the plurality of light sources can operate independently and only provide light therapy of a rough position and range.

In an embodiment, the fundus detection device is a fundus camera or an optical coherence tomography scanner.

In an embodiment, the optical system further includes a switch module coupled to the light source device, the switch module selectively turns on the light source device according to whether a specific area of the eye is scanned by the light scanning module, so as to track the specific position of the eye and shoot its image to avoid the effects of natural shaking of the eye.

In an embodiment, the optical system further includes an irradiation position control optical path and an irradiation range control lens configured to lock a specific area of the eye to be irradiated and shoot its image to avoid the effects of the natural shaking of the eye.

In an embodiment, the optical system further includes an analysis module and a feedback control module of the light scanning module configured to correct and synchronize coordinates of the optical coherence tomograph and coordinates of the light scanning module.

In an embodiment, the light intensity modulation module modulates the luminous intensity of the light source module correspondingly according to the thickness of each retinal layer of the eye analyzed by the optical coherence tomography scanner, so as to precisely control the dose of light therapy.

In an embodiment, the lens module controls the convergence and divergence of the therapy light according to the thickness of each retinal layer of the eye analyzed by the optical coherence tomography scanner, so as to precisely control the depth of light treatment.

Another preferred embodiment of the invention is an optical system operating method. In this embodiment, the optical system operating method includes steps of: (a) disposing a gaze module for an eye to gaze to fix a fundus of the eye; (b) emitting a therapy light to an eye; (c) modulating an intensity of the therapy light and controlling a depth of the therapy light; and (d) detecting the fundus to obtain a fundus image.

In an embodiment, when the light source module only comprises a single light source, the single light source needs to be matched with a light scanning module to modulate the therapy light to irradiate to a specific position and range of the eye.

In an embodiment, the step (b) is to emit the therapy light through a plurality of light sources arranged in an array, and the plurality of light sources can operate independently and only provide light therapy of a rough position and range.

In an embodiment, the step (b) is performed by a fundus camera or an optical coherence tomography scanner.

In an embodiment, the optical system operating method further includes a step of: selectively turning on the single light source according to whether a specific area of the eye is scanned by the light scanning module, so as to track a specific position of the eye and shoot its image to avoid the effects of natural shaking of the eye.

In an embodiment, the optical system operating method further includes a step of: disposing an irradiation position control optical path and an irradiation range control lens to lock a specific area of the eye to be irradiated and shoot its image to avoid the effects of the natural shaking of the eye.

In an embodiment, the optical system operating method further includes a step of: disposing an analysis module and a feedback control module of the light scanning module to correct and synchronize coordinates of the optical coherence tomograph and coordinates of the light scanning module.

In an embodiment, the optical system operating method further includes a step of: modulating the luminous intensity of the light source module correspondingly according to the thickness of each retinal layer of the eye analyzed by the optical coherence tomography scanner, so as to precisely control the dose of light therapy.

In an embodiment, the optical system operating method further includes a step of: controlling the convergence and divergence of the therapy light according to the thickness of each retinal layer of the eye analyzed by the optical coherence tomography scanner, so as to precisely control the depth of light treatment.

Compared to the prior art, the optical system and its operating method of the invention can scan the local area of the fundus, avoid the influence of natural eye shaking to lock the local position, make the low-intensity light source focus on the specific area and depth, and analyze the thickness of the target tissue layer of the retina by optical coherence tomography technology to adjust the appropriate light dose, and take pictures of the eye area before and after treatment to follow up the treatment effect, which effectively solves the problems that conventional phototherapy instruments can only roughly irradiate the entire eye, and unable to focus on localized areas of the eye or target delicate areas, unable to control the light dose according to the thickness of the tissue, and unable to directly use the same instrument to observe the treatment effect after the treatment is completed, so it can achieve five-dimensional (three-dimensional space, time, light dose) light treatment effect and the different retinal layers can also be treated with lights of different wavelengths.

The advantage and spirit of the invention may be understood by the following detailed descriptions together with the appended drawings.

BRIEF DESCRIPTION OF THE APPENDED DRAWINGS

FIG. 3 illustrates a flowchart of the optical system operating method in another embodiment of the invention.

FIG. 11 illustrates a flowchart of the optical system operating method correcting the light scanning module for detection the detection light and the therapy light in another embodiment of the invention.

FIG. 12 illustrates a block diagram of a light therapy light source.

DETAILED DESCRIPTION OF THE INVENTION

Figure 1:
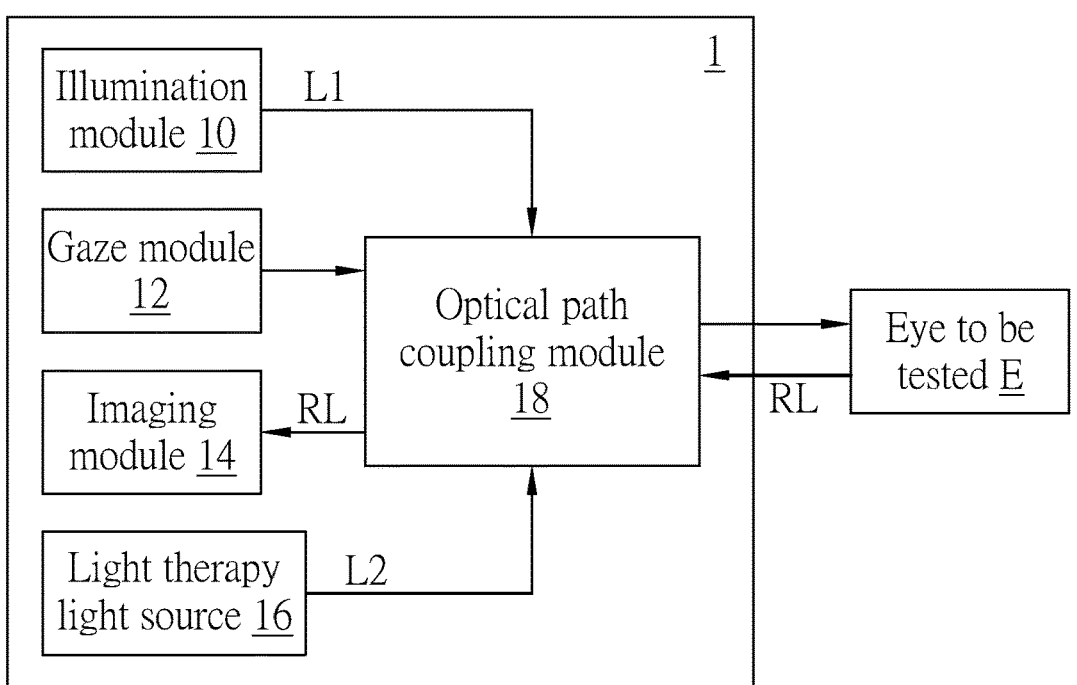
FIG. 1 illustrates a schematic diagram of the optical system in an embodiment of the invention.

Exemplary embodiments of the invention are referenced in detail now, and examples of the exemplary embodiments are illustrated in the drawings. Further, the same or similar reference numerals of the components in the drawings and the detailed description of the invention are used on behalf of the same or similar parts.

The invention provides an optical system related to the treatment of eye diseases and an operating method thereof, which can integrate a phototherapy device using photodynamic therapy and low-level laser therapy and a fundus detection optical path (fundus camera, optical coherence tomography) to achieve specific area or precise position-locked irradiation, control the light dose, capture fundus images and structural data after phototherapy, so as to track the treatment effect and effectively solve the problems encountered by the previous technology.

A preferred embodiment of the invention is an optical system. In this embodiment, the optical system includes a light source device, a gaze module and a fundus detection device. The light source device includes a light source module, a light intensity modulation module and a lens module. The light source module is used to emit a therapy light to an eye. The light intensity modulation module is used to modulate an intensity of the therapy light. The lens module is used to control a depth of the therapy light. The gaze module is used to be gazed by the eye to fix a fundus of the eye. The fundus detection device and the light source device are integrated to detect the fundus to obtain a fundus image.

In fact, the fundus detection device can be a fundus camera or an optical coherence tomography scanner, but not limited to this. The light intensity modulation module can modulate the luminous intensity of the light source module correspondingly according to the thickness of each retinal layer of the eye analyzed by the optical coherence tomography scanner, so as to precisely control the dose of light therapy, but not limited to this.

In fact, the light source module can only include a single light source or a plurality of light sources arranged in an array. When the light source module only includes a single light source, the single light source needs to be matched with a light scanning module to modulate the therapy light to irradiate to a specific position and range of the eye. When the light source module includes a plurality of light sources arranged in an array, the plurality of light sources can operate independently and only provide light therapy of a rough position and range.

In another embodiment, the optical system can further include a switch module. The switch module is coupled to the light source device. The switch module can selectively turn on the light source device according to whether a specific area of the eye is scanned by the light scanning module, so as to track the specific position of the eye and shoot its image to avoid the effects of natural shaking of the eye.

In another embodiment, the optical system can further include an irradiation position control optical path and an irradiation range control lens configured to lock a specific area of the eye to be irradiated and shoot its image to avoid the effects of the natural shaking of the eye, but not limited to this.

In another embodiment, the optical system can further include an analysis module and a feedback control module of the light scanning module configured to correct and synchronize coordinates of the optical coherence tomograph and coordinates of the light scanning module, but not limited to this.

Please refer to FIG. 1. FIG. 1 illustrates a schematic diagram of an optical system according to an embodiment of the invention. As shown in FIG. 1, the optical system 1 includes an illumination module 10, a gaze module 12, an imaging module 14, a light therapy light source 16 and an optical path coupling module 18. The illumination module 10, the gaze module 12 and the light therapy light source 16 are respectively coupled to the light path coupling module 18. The optical path coupling module 18 is coupled to the imaging module 14. The gaze module 12 is used for the eye E to be tested to watch, so that the orientation of the fundus of the eye E to be tested can be fixed. The light therapy light source 16 provides a therapy light L2 to the light path coupling module 18 and the light path coupling module 18 emits the therapy light L2 to the fundus of the eye E to be tested for light therapy. The illumination module 10 provides an illumination light L1 to the light path coupling module 18 and the light path coupling module 18 emits the illumination light L1 to the fundus of the eye E to be tested. The fundus of the eye E to be tested reflects the illumination light L1 to form a reflected light RL and the reflected light RL is emitted to the imaging module 14 through the optical path coupling module 18, so that the imaging module 14 can capture the fundus image of the eye E to be tested.

Figure 2:
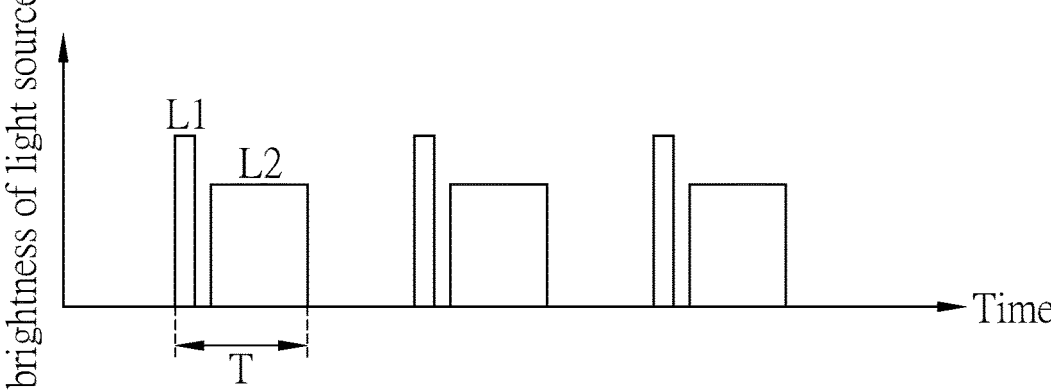
FIG. 2 illustrates a timing diagram that when the therapy light and the illumination light share the same light source, the brightness of the light source is rapidly switched in the same treatment cycle to achieve effects of treatment and imaging lighting.

Please refer to FIG. 2. It is assumed that the illumination light L1 and the therapy light L2 are provided by the same light source (such as infrared light), the light source can be quickly switched to provide the illumination light L1 with higher brightness or the therapy light L2 with lower brightness at different working times in the same treatment period T, so that the illumination light L1 and the therapy light L2 can be provided at different working times respectively, so it can have both therapy and imaging lighting effects.

Please refer to FIG. 3. FIG. 3 illustrates a flowchart of the optical system operating method in another embodiment of the invention. As shown in FIG. 3, the optical system operating method can include the following steps:

Step S10: the eye E to be tested watching the gaze module 12 to fix the orientation of the fundus of the eye E to be tested;

Step S12: the light therapy light source 16 emitting the therapy light L2 to the eye E to be tested;

Step S14: turning off the light therapy light source 16;

Step S16: turning on the illumination module 10 to emit the illumination light L1 to illuminate the fundus of the eye E to be tested; and Step S18: the imaging module 14 capturing the fundus image of the eye E to be tested.

For example, when the light source of the gaze module 12 is turned on, the subject's eye E to be tested watches the light source of the gaze module 12 to fix the orientation of the fundus of the eye E to be tested. Next, turning on single or multiple light sources in the light therapy light source 16 and moving one or more lenses or mirrors in the optical path coupling module 18 to adjust the range and position of the therapy light L2 emitted by the light therapy light source 16 to the fundus of the eye E to be tested. After the course of the light therapy is over, before the fundus image is captured, if the imaging module 14 does not include a filter for the wavelength used by the light therapy light source 16, the light therapy light source 16 is turned off. Next, the illumination module 10 is turned on to emit the illumination light L1 to the fundus of the eye E to be tested, and the imaging module 14 captures the fundus image of the eye E to be tested.

Figure 4:
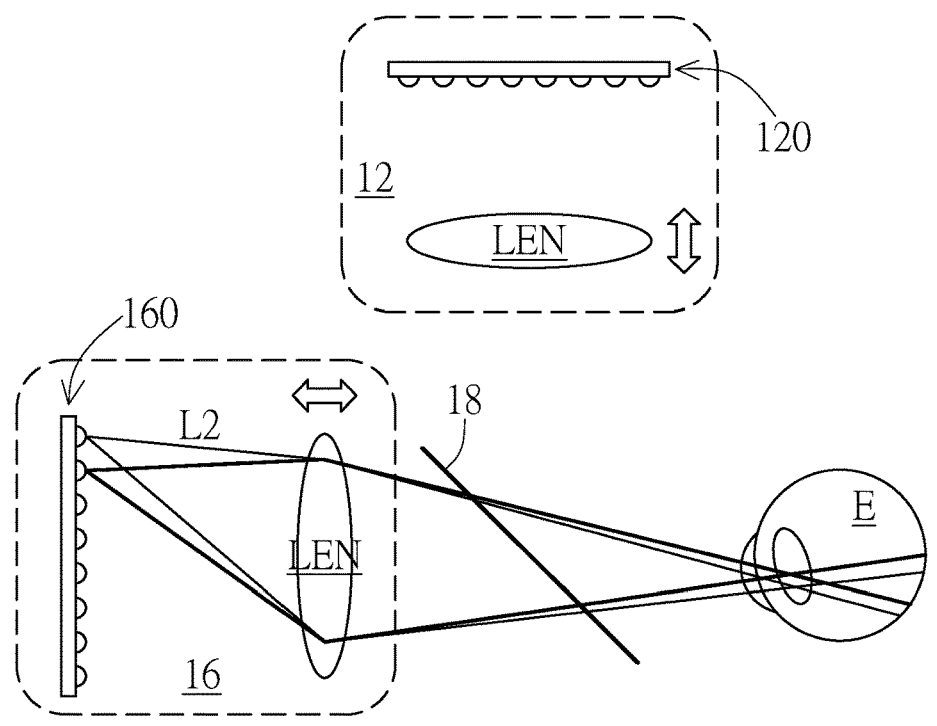
FIG. 4 illustrates an optical path schematic diagram of the light therapy light source, gaze module, optical path coupling module and the eye to be tested.

Please refer to FIG. 4. FIG. 4 illustrates a schematic diagram of the light path of the light therapy light source 16, the gaze module 12, the light path coupling module 18 and the eye E to be tested.

As shown in FIG. 4, the gaze module 12 includes a light source 120 and a lens LEN that can move up and down. The light therapy light source 16 includes a light source 160 and a lens LEN that can move left and right, which is used for the eye E to be tested to watch, so as to fix the orientation of the fundus of the eye E to be tested. The therapy light L2 emitted by the light source 160 is refracted by the lens LEN and then emitted to the eye E to be tested through the optical path coupling module 18 to perform light therapy.

It should be noted that, FIG. 4 is the common optical path design of fundus camera: the therapy light L2 emitted by the point light source 160 of the light therapy light source 16 is converged on the pupil plane of the eye E to be tested through the optical path coupling module 18, and then diffusely irradiated to the fundus of the eye E to be tested. The light path coupling module 18 can be composed of a plurality of lenses, lens arrays and mirrors, so as to achieve the effect of individually controlling the range and position of the light therapy light source 16 irradiating the fundus. The light path between the light therapy light source 16, the light path coupling module 18 and the eye E to be tested is not limited to this. The light sources 120 of the gaze module 12 are respectively disposed at different positions, and the light sources 120 at different positions can be lit up for the eye E to watch and the angle of the eye E to be tested can be adjusted accordingly.

Figure 5:
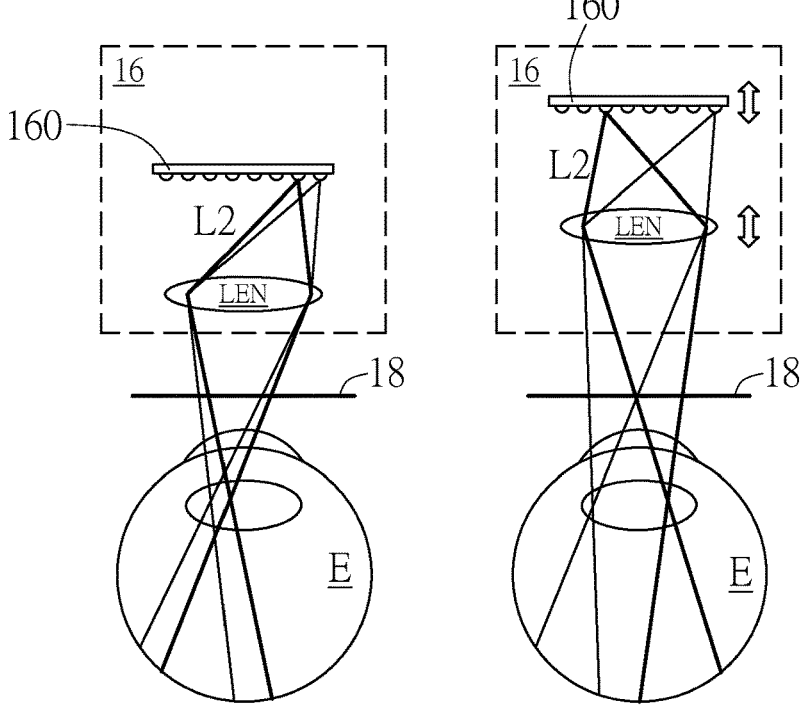
FIG. 5 illustrates a schematic diagram that the therapy light source and the optical path coupling module can be manually/automatically adjusted by mechanical linkage when combined with a wearable device.

Please refer to FIG. 5, when the optical system of the invention is combined with the wearable device, the light therapy light source 16 and the optical path coupling module 18 can be manually/automatically adjusted by mechanical linkage, and the light therapy light source 16 can also be controlled by DLP technology. The therapy light L2 emitted from the light therapy light source 16 is projected onto the area of the fundus of the eye E to be tested.

Figure 6:
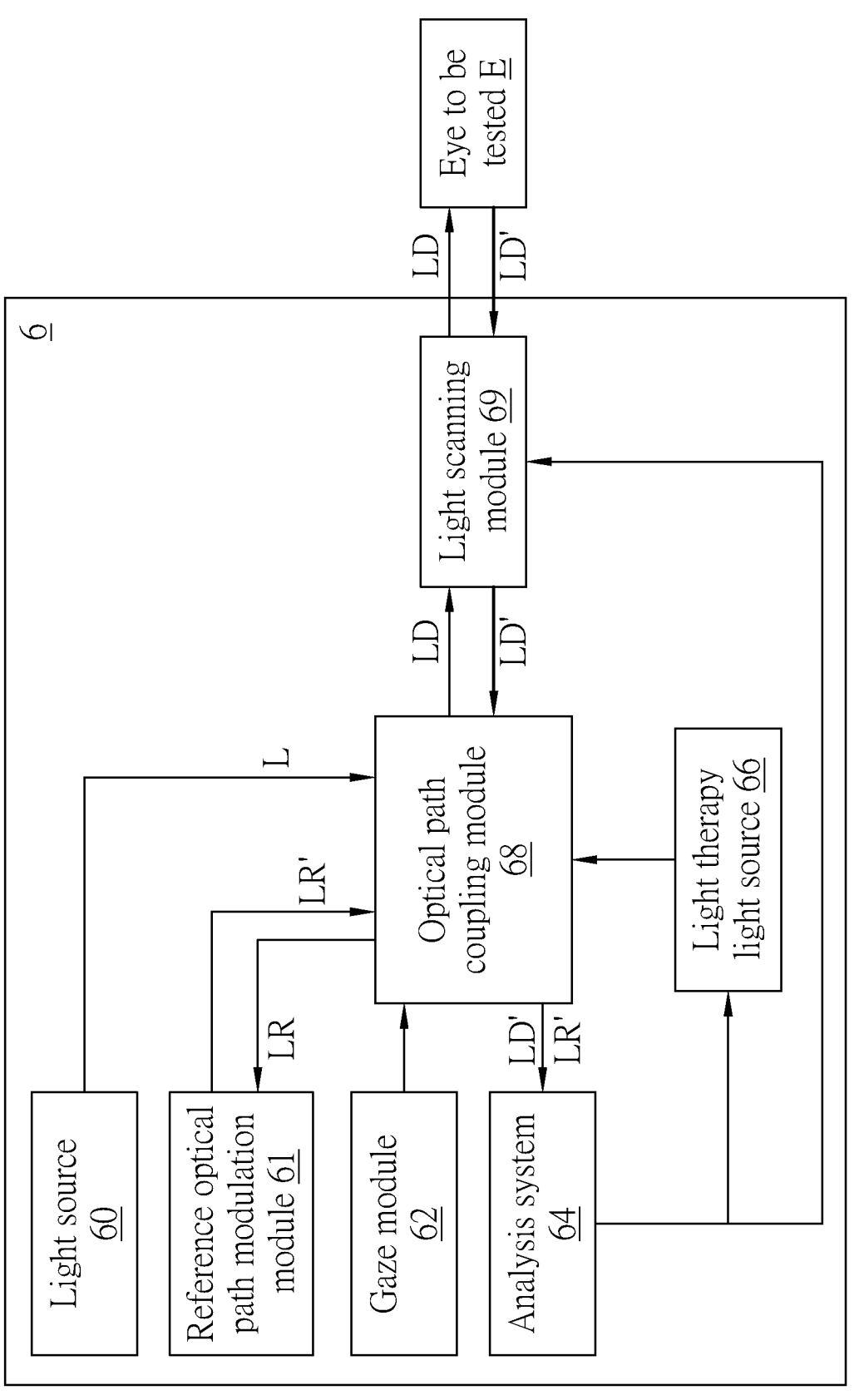
FIG. 6 illustrates a schematic diagram of the optical system in another embodiment of the invention.

Please refer to FIG. 6. FIG. 6 illustrates a schematic diagram of the optical system in another embodiment of the invention. As shown in FIG. 6, the optical system 6 includes a light source 60, a reference optical path modulation module 61, a gaze module 62, an analysis system 64, a light therapy light source 66, an optical path coupling module 68 and a light scanning module 69. The light source 60, the reference light optical path modulation module 61, the gaze module 62, the analysis system 64, the light therapy light source 66 and the light scanning module 69 are all coupled to the optical path coupling module 68. The analysis system 64 is respectively coupled to the light therapy light source 66, the light path coupling module 68 and the light scanning module 69. The light scanning module 69 is disposed between the light path coupling module 68 and the eye E to be tested.

The light source 60 provides a light L required for optical coherence tomography, and when the light L enters the optical path coupling module 68, it is divided into a detection light LD and a reference light LR. The detection light LD enters the light scanning module 69 and is guided to a specific position of the eye E to be tested, and then is reflected back to the light path coupling module 68. The reference light LR enters the reference light optical path modulation module 61 to adjust the optical path and is reflected back to the optical path coupling module 68. The reflected detection light LD' and the reflected reference light LR' are interfered and analyzed by the analysis system 64 to obtain the fundus structure of the specific position of the eye E to be tested.

The gaze module 62 provides a target for the eye E to watch, and the gaze module 62 can be formed by an LCD panel or a plurality of LEDs. By modulating the different positions of the gaze light spot, the gaze angle of the eye E to be tested is changed, so as to facilitate the detection light LD and the therapy light L2 are emitted to the selected area of the eye E to be tested. The analysis system 64 records and analyzes the current scanning site and the to-be-scanned site. When the selected area is about to be scanned, the light therapy light source 66 is turned on. When leaving the selected area, the light therapy light source 66 is turned off.

In addition, the analysis system 64 can control the light scanning module 69 to lock the scanning area. The detection light LD and the therapy light L2 may or may not share the light scanning module 69. If the light scanning module 69 is shared, the light therapy light source 66 needs to be turned off/on when the scanning position leaves/enters the selected area. If the light scanning module 69 is not shared, the detection light LD scans the fundus of the eye E to be tested to confirm the movement of the fundus and track the selected area, and the light therapy light source 66 can use the independent light scanning module 69 to continuously illuminate the selected area. And, the independent light scanning module 69 can add a lens to adjust the irradiation range of the light therapy light source 66.

Figure 7:
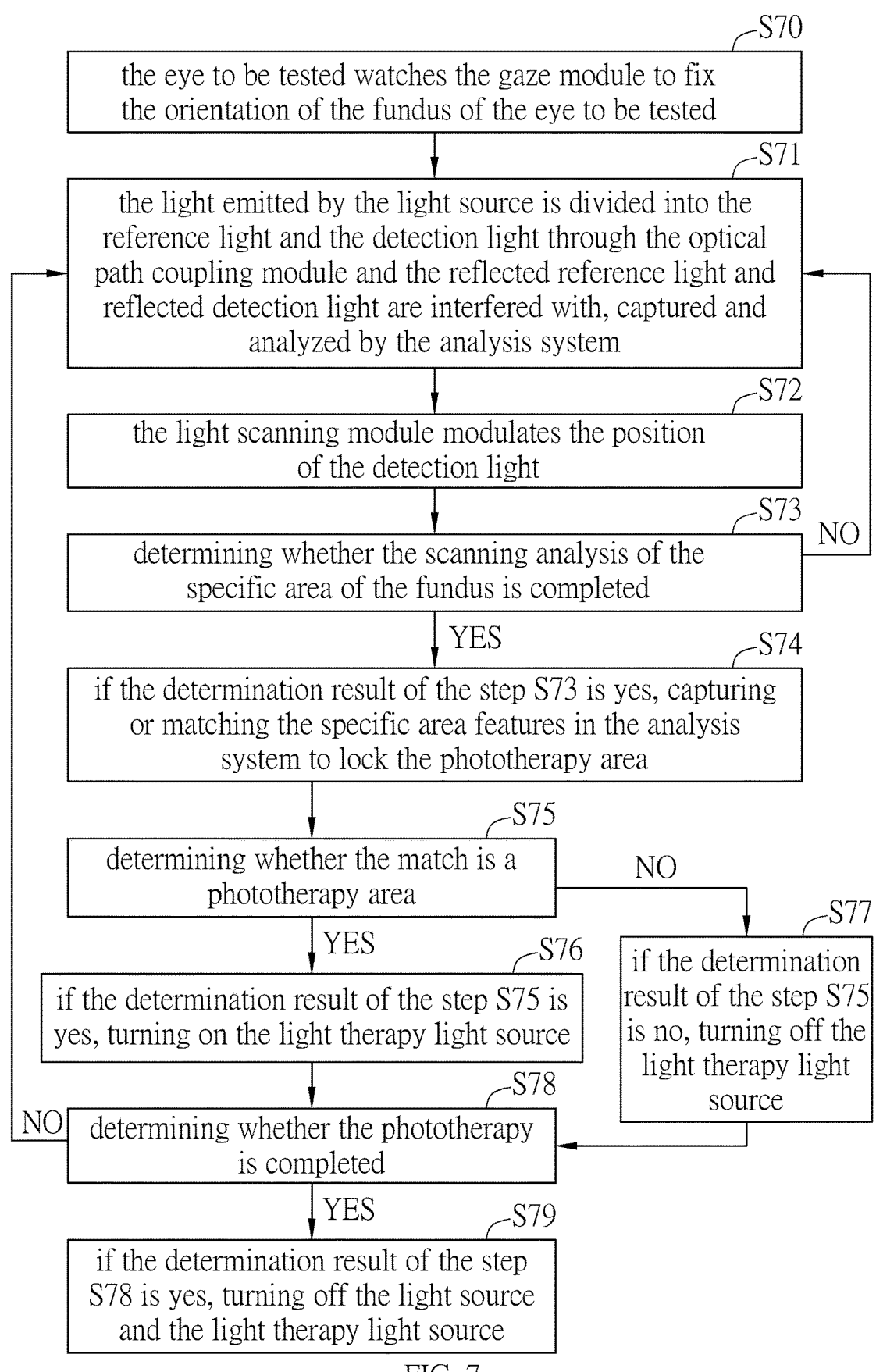
FIG. 7 illustrates a flowchart of the optical system operating method in another embodiment of the invention.

Please refer to FIG. 7. FIG. 7 illustrates a flowchart of the optical system operating method in another embodiment of the invention. As shown in FIG. 7, the optical system operating method can include the following steps:

Step S70: the eye E to be tested watches the gaze module 62 to fix the orientation of the fundus of the eye E to be tested;

Step S71: the light emitted by the light source 60 is divided into the reference light LR and the detection light LD through the optical path coupling module 68. The reference light LR enters the reference light optical path modulation module 61 to adjust the optical path and is reflected back to the optical path coupling module 68. The detection light LD enters the fundus of the eye E to be tested and is reflected back to the optical path coupling module 68. The reflected probe light LD' and the reflected reference light LR' are interfered with, captured and analyzed by the analysis system 64;

Step S72: the light scanning module 69 modulates the position of the detection light LD;

Step S73: determining whether the scanning analysis of the specific area of the fundus is completed;

Step S74: if the determination result of the step S73 is yes, capturing or matching the specific area features in the analysis system 64 to lock the phototherapy area;

If the determination result of the step S73 is no, then return to the step S71;

Step S75: determining whether the match is a phototherapy area;

Step S76: if the determination result of the step S75 is yes, turning on the light therapy light source;

Step S77: if the determination result of the step S75 is no, turning off the light therapy light source;

Step S78: determining whether the phototherapy is completed;

Step S79: if the determination result of the step S78 is yes, turning off the light source and the light therapy light source; and If the determination result of step S78 is no, then go back to step S71.

For example, when the light source of the gaze module 62 is turned on, the subject's eye E to be tested watches the light source of the gaze module 62 to fix the orientation of the fundus of the eye E to be tested. Next, the optical coherence tomography of the fundus was started and the characteristics of the fundus were analyzed. When the analysis system 64 selects the area to be locked, the analysis system 64 continuously detects the movement direction of the area, changes the position scanned by the light scanning module 69 to perform area locking. When the scanning position leaves/enters the selected area, the light therapy light source needs to be turned off/on. In addition, because the optical coherence tomography can obtain the blood vessel distribution map of the fundus, it can be used as the identification of individual retinal characteristics. During the scanning process, the analysis system can go to the database to extract the historical scanning records of the subjects, track the historical treatment site and curative effect, and analyze whether there are new features (possibly new symptoms).

Figure 8:
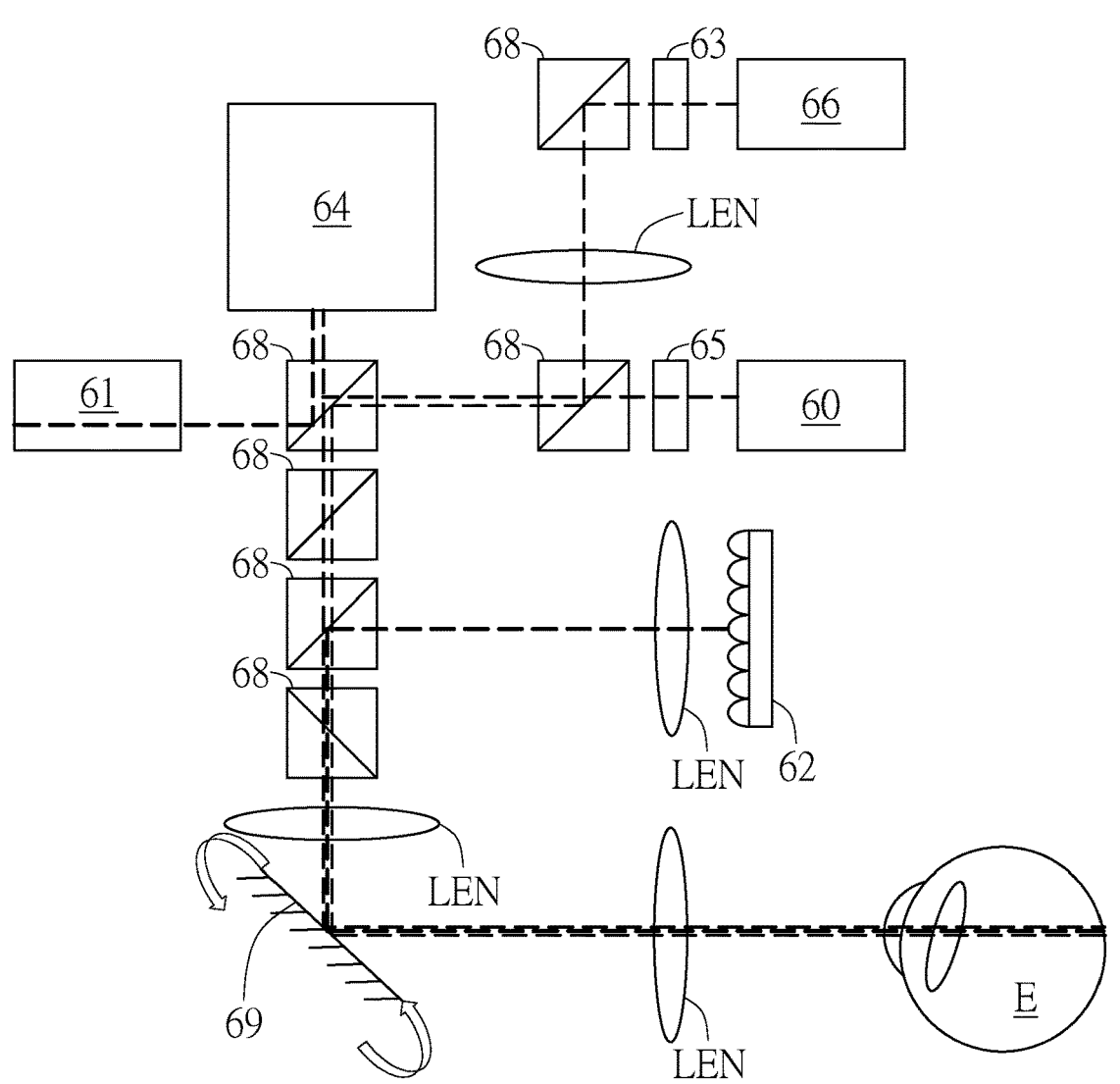
FIG. 8 illustrates an optical path schematic diagram that the detection light source and the light therapy light source share the scanning module.

Please refer to FIG. 8. FIG. 8 illustrates a schematic diagram of the optical path when the detection light source 60 and the light therapy light source 66 share the same detection light beam scanning module 69. As shown in FIG. 8, a switch 63 is added to the optical coherence tomography optical path. When the system scans the local area of the eye E to be tested, the light therapy light source 66 is turned on, and when the system leaves the local area of the eye E to be tested, the light therapy light source 66 is turned off. Thereby, the effect of treating and improving the disease of the part of the eye E to be tested can be achieved when scanning the local area of the eye E to be tested.

Figure 9A:
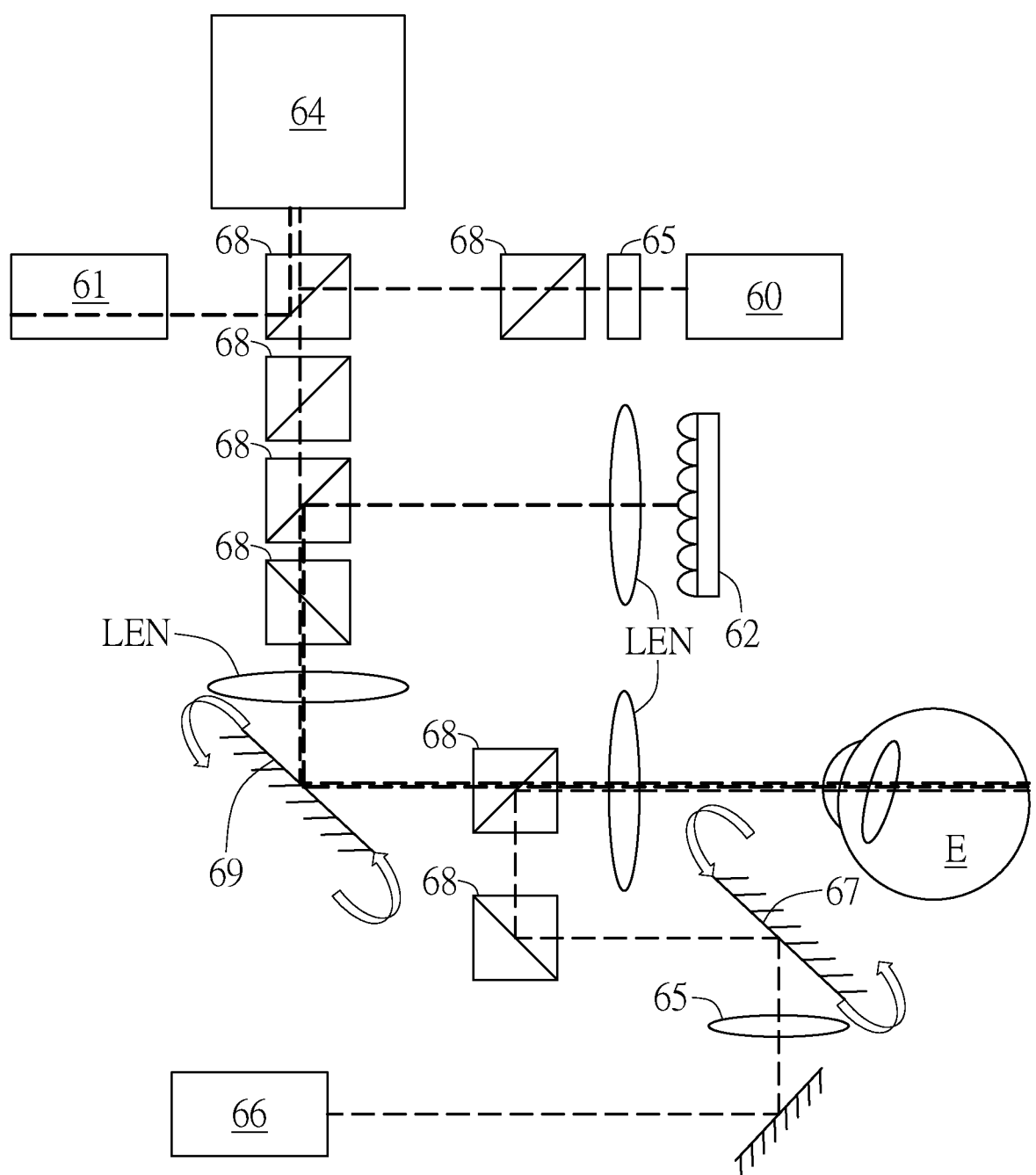
FIG. 9A illustrates an optical path schematic diagram that the detection light source and the light therapy light source do not share the scanning module.

Please refer to FIG. 9A. FIG. 9A illustrates a schematic diagram of the light path when the detection light source 60 and the light therapy light source 66 do not share the scanning module 69. As shown in FIG. 9A, a therapy light scanning module 67 is added to the optical path of optical coherence tomography, so that the effects of using the detection light scanning module 69 to scan the local area of the eye E to be tested and using the therapy light scanning module 67 to treat diseases in another local area of the eye E to be tested can be achieved.

Figure 9B:
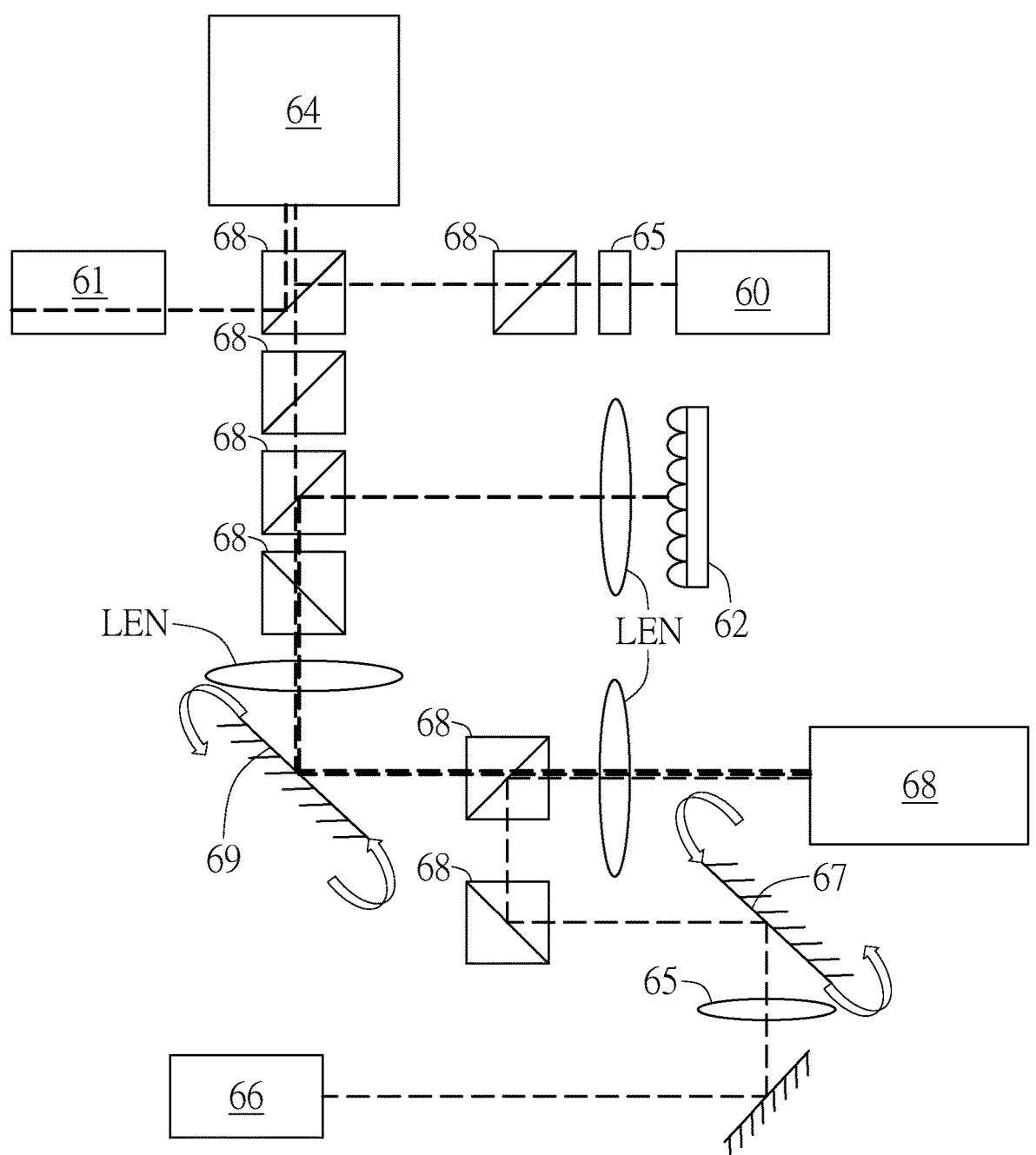
FIG. 9B illustrates an optical path schematic diagram of using the photosensitive module to perform position correction on the detection light beam scanning module and the therapy light beam scanning module.
Figure 10:
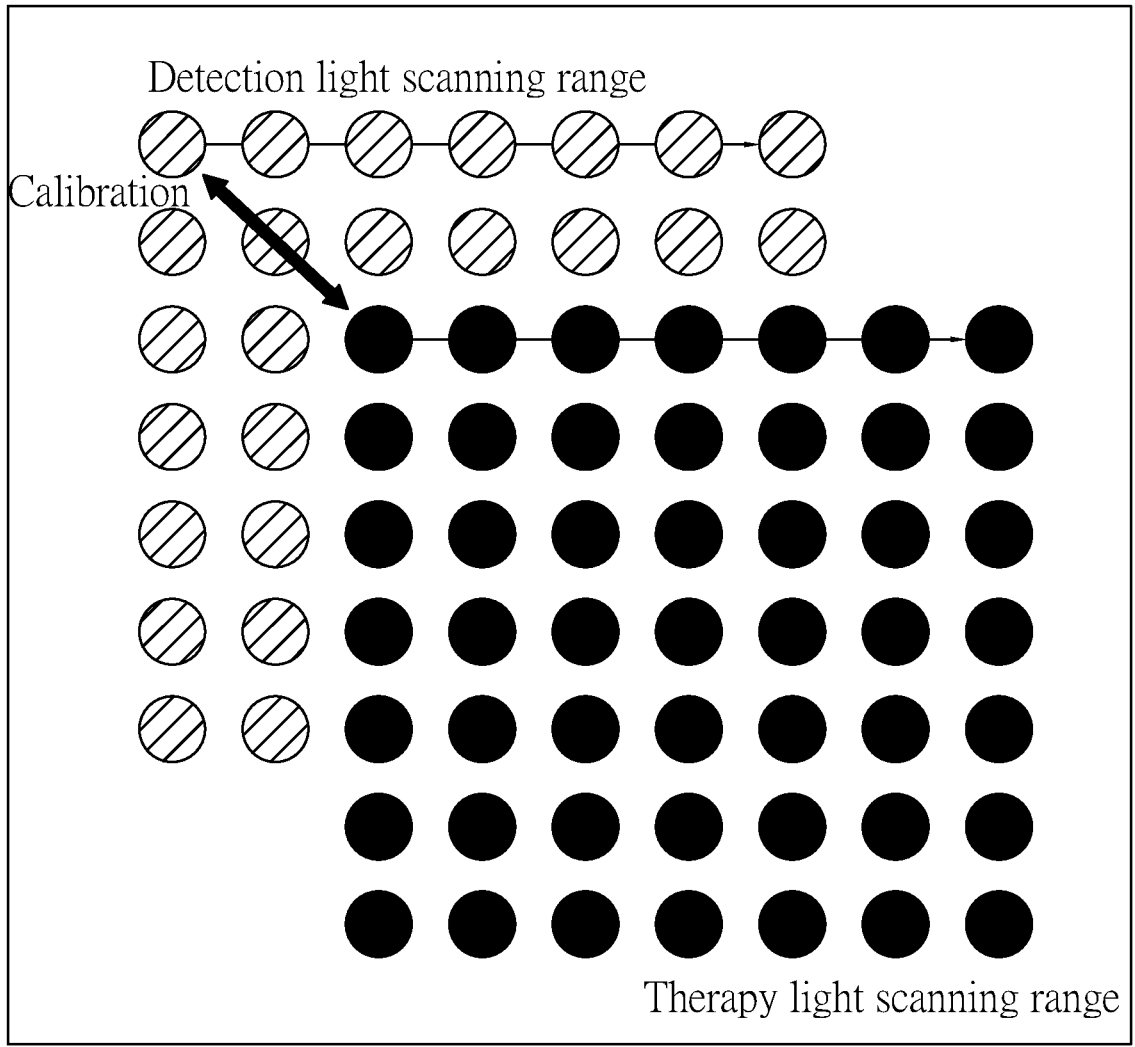
FIG. 10 illustrates a schematic diagram of the range of light spots scanned by the detection light and the therapy light on the photosensitive module.

Please refer to FIG. 9B and FIG. 10. FIG. 9B illustrates a schematic diagram of the optical path required for position correction of the detection light scanning module 69 and the therapy light scanning module 67 using the photosensitive module 68. FIG. 10 illustrates a schematic diagram of the range of light spots scanned by the detection light and the therapy light on the photosensitive module 68, which can be used to correct the positions of the detection light scanning module 69 and the therapy light scanning module 67.

In practical applications, before starting to use the eye E to be tested, it is necessary to perform calibration of the control position range of the detection light scanning module 69 and the therapy light scanning module 67, so that the detection light and the therapy light can be adjusted. Different areas within the eye E to be tested are scanned separately.

For example, the calibration method can include the following steps: using the photosensitive module 68 to detect the detection light and the therapy light; after leaving a series of light spot ranges, we can know the coordinates of the moving range of the detection light scanning module 69. Afterwards, the therapy light scanning module 67 is used to move the therapy light, and another series of light spot ranges can be left in the field of view of the photosensitive module 68, so that the coordinates of the moving range of the therapy light scanning module 67 can be known. Finally, these two sets of coordinates are aligned to complete the calibration.

Please refer to FIG. 11. FIG. 11 illustrates a flowchart of the optical system operating method for calibrating the light scanning module of the detection light/therapy light according to another embodiment of the invention. As shown in FIG. 11, the optical system operating method can include the following steps:

Step S110: the photosensitive module 68 that can detect the detection light and the therapy light is disposed in the optical path, and is ready to start calibration;

Step S112: moving the detection light with the detection light scanning module 69, scanning a series of light spots on the photosensitive module 68 in sequence, and recording the coordinates of the detection light scanning range;

Step S114: using the therapy light scanning module 67 to move the therapy light, scanning a series of light spots on the photosensitive module 68 in sequence, and recording the coordinates of the therapy light scanning range;

Step S116: recording the coordinates of the scanning range of the detection light and the coordinates of the scanning range of the therapy light and aligning the two to complete the calibration; and Step S118: the therapy light scanning module 67 can move independently of the detection light scanning module 69 to treat a specific position within the visual field of the eye E to be tested.

It should be noted that, in order to make the therapy light energy move independently of the detection light during treatment, it is necessary to use the photosensitive module 68 to measure the coordinates of the spot movement range of the detection light scanning module 69, and then measure t the coordinates of the moving range of the light spot of the therapy light scanning module 67, and finally align the two sets of coordinates to complete the calibration. In this way, the corrected therapy light scanning module 67 can move independently of the detection light scanning module 69 to treat diseases at a specific position within the visual field of the eye E to be tested.

Referring to FIG. 12, in one embodiment, the light therapy light source 66 can include a light source 660, a light intensity modulation module 662 and a lens module 664. The light source 660 can be a single light source or an array of light sources. The light intensity modulation module 662 can change the intensity of the therapy light entering the lens module 664 by means of liquid crystal or adjusting the polarization of the light source. The lens module 664 can adjust the contraction and divergence of the therapy light, and provide another degree of freedom to control the irradiation range of the fundus irradiated on the eye E to be tested.

Compared to the prior art, the optical system and its operating method of the invention can scan the local area of the fundus, avoid the influence of natural eye shaking to lock the local position, make the low-intensity light source focus on the specific area and depth, and analyze the thickness of the target tissue layer of the retina by optical coherence tomography technology to adjust the appropriate light dose, and take pictures of the eye area before and after treatment to follow up the treatment effect, which effectively solves the problems that conventional phototherapy instruments can only roughly irradiate the entire eye, and unable to focus on localized areas of the eye or target delicate areas, unable to control the light dose according to the thickness of the tissue, and unable to directly use the same instrument to observe the treatment effect after the treatment is completed, so it can achieve five-dimensional (three-dimensional space, time, light dose) light treatment effect and the different retinal layers can also be treated with lights of different wavelengths.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical system, comprising:

a light source device comprising a light source module, a light intensity modulation module and a lens module, wherein the light source module is configured to emit a therapy light to an eye, the light intensity modulation module is configured to modulate an intensity of the therapy light, the lens module is configured to control a depth of the therapy light; and a gaze module configured to be gazed by the eye to fix a fundus of the eye; and a fundus detection device integrated with the light source device and configured to detect the fundus to obtain a fundus image, wherein the light source module comprises a plurality of light sources arranged in an array, and the plurality of light sources operate independently and provide light therapy of a rough position and range.

2. The optical system of claim 1, wherein when the light source module only comprises a single light source, the single light source needs to be matched with a light scanning module to modulate the therapy light to irradiate to a specific position and range of the eye.

3. The optical system of claim 1, wherein the fundus detection device is a fundus camera or an optical coherence tomography scanner.

4. The optical system of claim 2, further comprising a switch module coupled to the light source device, the switch module selectively turns on the light source device according to whether a specific area of the eye is scanned by the light scanning module, so as to track the specific position of the eye and shoot an image of the specific position of the eye to avoid effects of natural shaking of the eye.

5. The optical system of claim 3, further comprising an analysis module and a feedback control module of the light scanning module configured to correct and synchronize coordinates of the optical coherence tomograph and coordinates of the light scanning module.

6. The optical system of claim 3, wherein the light intensity modulation module modulates a luminous intensity of the light source module correspondingly according to a thickness of each retinal layer of the eye analyzed by the optical coherence tomography scanner, so as to precisely control a dose of light therapy.

7. The optical system of claim 1, further comprising an irradiation position control optical path and an irradiation range control lens configured to lock a specific area of the eye to be irradiated and shoot an image of the specific area of the eye to avoid the effects of the natural shaking of the eye.

8. The optical system of claim 3, wherein the lens module controls the convergence and divergence of the therapy light according to the thickness of each retinal layer of the eye analyzed by the optical coherence tomography scanner, so as to precisely control the depth of light treatment.

9. An optical system comprising:
   a light source device comprising:
      a light source module configured to emit a therapy light to an eye and only comprising a single light source matched with a light scanning module to modulate the therapy light to irradiate to a specified position and range of the eye;
      a light intensity modulation module configured to modulate an intensity of the therapy light; and
      a lens module configured to control a depth of the therapy light;
   a gaze module configured to be gazed by the eye to fix a fundus of the eye;
   a fundus detection device integrated with the light source device and configured to detect the fundus to obtain a fundus image, wherein the light source module only comprises a single light source matched with a light scanning module to modulate the therapy light to irradiate to a specific position and range of the eye; and
   a switch module coupled to the light source device, the switch module selectively turns on the light source device according to whether a specific area of the eye is scanned by the light scanning module to track the specific position of the eye and shoot an image of the specific position of the eye to avoid the effects of natural shaking of the eye.

10. The optical system of claim 9, wherein the fundus detection device is a fundus camera or an optical coherence tomography scanner.

11. The optical system of claim 10, further comprising an analysis module and a feedback control module of the light scanning module configured to correct and synchronize coordinates of the optical coherence tomograph scanner and coordinates of the light scanning module.

12. The optical system of claim 10, wherein the light intensity modulation module modulates the luminous intensity of the light source module correspondingly according to the thickness of each retinal layer of the eye analyzed by the optical coherence tomography scanner, so as to precisely control the dose of light therapy.

13. The optical system of claim 10, wherein the lens module controls the convergence and divergence of the therapy light according to the thickness of each retinal layer of the eye analyzed by the optical coherence tomography scanner, so as to precisely control the depth of light treatment.

14. The optical system of claim 9, further comprising an irradiation position control optical path and an irradiation range control lens configured to lock a specific area of the eye to be irradiated and shoot its image to avoid the effects of the natural shaking of the eye.

15. An optical system, comprising:
   a light source device comprising:
      a light source module configured to emit a therapy light to an eye;
      a light intensity modulation module configured to modulate an intensity of the therapy light; and
      a lens module configured to control a depth of the therapy light;
   a gaze module configured to be gazed by the eye to fix a fundus of the eye;
   a fundus detection device integrated with the light source device and configured to detect the fundus to obtain a fundus image; and
   an irradiation position control optical path and an irradiation range control lens configured to lock a specific area of the eye to be irradiated and shoot an image of the specific area of the eye to avoid the effects of the natural shaking of the eye.

16. The optical system of claim 15, wherein when the light source module only comprises a single light source, the single light source is matched with a light scanning module to modulate the therapy light to irradiate to a specific position and range of the eye.

17. The optical system of claim 15, wherein the fundus detection device is a fundus camera or an optical coherence tomography scanner.

18. The optical system of claim 17, further comprising an analysis module and a feedback control module of the light scanning module configured to correct and synchronize coordinates of the optical coherence tomograph and coordinates of the light scanning module.

19. The optical system of claim 17, wherein the light intensity modulation module modulates the luminous intensity of the light source module correspondingly according to the thickness of each retinal layer of the eye analyzed by the optical coherence tomography scanner, so as to precisely control the dose of light therapy.

20. The optical system of claim 17, wherein the lens module controls the convergence and divergence of the therapy light according to the thickness of each retinal layer of the eye analyzed by the optical coherence tomography scanner, so as to precisely control the depth of light treatment.

* * * * *